(12) United States Patent
Kusakabe (10) Patent No.: US 8,870,824 B2
(45) Date of Patent: Oct. 28, 2014

(54) ASPIRATION CATHETER

(75) Inventor: Susumu Kusakabe, Kakamigahara (JP)

(73) Assignees: Terumo Kabushiki Kaisha, Tokyo (JP); Terumo Clinical Supply Co., Ltd., Kakamigahara-Shi, Gifu (JP)

( * ) Notice: Subject to any disclaimer, the term of this patent is extended or adjusted under 35 U.S.C. 154(b) by 286 days.

(21) Appl. No.: 13/183,806

(22) Filed: Jul. 15, 2011

(65) Prior Publication Data

US 2012/0016344 A1  Jan. 19, 2012

Related U.S. Application Data

(60) Provisional application No. 61/367,054, filed on Jul. 23, 2010.

(30) Foreign Application Priority Data

Jul. 16, 2010 (JP) ................................ 2010-162198
May 20, 2011 (JP) ................................ 2011-113567

(51) Int. Cl.
*A61M 5/178* (2006.01)
*A61M 25/00* (2006.01)
*A61M 31/00* (2006.01)
*A61M 25/01* (2006.01)

(52) U.S. Cl.
CPC ....... *A61M 25/0021* (2013.01); *A61M 25/0108* (2013.01); *A61M 25/005* (2013.01); *A61M 25/0009* (2013.01); *A61M 25/0023* (2013.01); *A61M 2025/0183* (2013.01)
USPC ................ 604/164.13; 604/164.01; 604/528; 604/93.01

(58) Field of Classification Search
CPC ............ A61M 2025/0183; A61M 2025/0004; A61M 25/0021; A61M 25/00; A61M 25/01; A61M 25/0043; A61M 25/0023

USPC ......... 604/524, 507, 508, 510, 95.04, 103.04, 604/528, 164.01, 164.13, 93.01, 523
See application file for complete search history.

(56) References Cited

U.S. PATENT DOCUMENTS 5,419,774 A * 5/1995 Willard et al. .................. 604/22
6,152,909 A  11/2000 Bagaoisan et al.
(Continued)

FOREIGN PATENT DOCUMENTS

EP  1 518 582 A1  3/2005
EP     2138200   *  4/2008
(Continued)

OTHER PUBLICATIONS

Extended European Search Report dated Oct. 31, 2011, issued by the European Patent Office in the corresponding European Application No. 11174255.7. (10 pages).

*Primary Examiner* — Kevin C Sirmons
*Assistant Examiner* — Bradley G Thomas, Jr.
(74) *Attorney, Agent, or Firm* — Buchanan Ingersoll & Rooney PC (57) ABSTRACT

An aspiration catheter includes an aspiration tube and an aspiration lumen extending between and opening to the distal and proximal ends of the aspiration tube, and a guidewire tube bonded to the outer surface of the aspiration tube on a distal end portion of the aspiration tube, with at least a portion of the guidewire tube being parallel to the aspiration tube. A guidewire lumen extends through the guidewire tube and opens at a proximal opening located at a proximal end of the guidewire tube. The outer surface of the aspiration tube has a flat portion where the outer surface is parallel to an axial direction of the aspiration lumen, and the proximal opening of the guidewire lumen is located at the flat portion of the outer surface of the aspiration tube.

22 Claims, 8 Drawing Sheets

(56) References Cited

U.S. PATENT DOCUMENTS

| | | |
|---|---|---|
| 7,244,250 B2 | 7/2007 | Miki et al. |
| 7,250,042 B2 * | 7/2007 | Kataishi et al. ............... 604/524 |
| 7,294,117 B2 | 11/2007 | Provost-tine et al. |
| 7,608,063 B2 | 10/2009 | Le et al. |
| 2002/0177800 A1 * | 11/2002 | Bagaoisan et al. ........... 604/6.12 |
| 2005/0070847 A1 * | 3/2005 | van Erp et al. ........... 604/103.04 |
| 2007/0106211 A1 * | 5/2007 | Provost-Tine et al. ..... 604/96.01 |
| 2009/0240206 A1 * | 9/2009 | Lunn et al. .................... 604/175 |
| 2009/0270800 A1 | 10/2009 | Spurchise et al. |

FOREIGN PATENT DOCUMENTS

| | | |
|---|---|---|
| EP | 2 138 200 A1 | 12/2009 |
| JP | 2006-297063 A | 11/2006 |
| JP | 2010-057831 A | 3/2010 |
| WO | WO 2007/050296 A1 | 5/2007 |

\* cited by examiner

ASPIRATION CATHETER

This application claims priority under 35 U.S.C. §119(e) to U.S. Provisional Application No. 61/367,054 filed on Jul. 23, 2010, and claims priority under 35 U.S.C. §119(a) to Japanese Application No. 2010-162198 filed on Jul. 16, 2010 and Japanese Application No. 2011-113567 filed on May 20, 2011, the entire content of all three of which is incorporated herein by reference.

TECHNOLOGICAL FIELD

The present invention generally pertains to an aspiration catheter for removing, by aspiration, a foreign body such as thrombus produced in a blood vessel through an aspiration lumen.

BACKGROUND DISCUSSION

A treatment method for removing a foreign body such as thrombus clogging a blood vessel involves use of an aspiration catheter having a long shaft formed therein with an aspiration lumen.

An aspiration catheter, in general, has a guidewire lumen in which a guidewire preceding in a living body is inserted and passed, and the aspiration catheter itself is inserted to a target part while being guided by the guidewire. Then, by a negative pressure generated by aspiration means such as a syringe connected to a hub provided at the proximal end of the aspiration catheter, the foreign body can be aspirated via an aspiration port at the distal end of the aspiration catheter into the aspiration lumen and be removed to the exterior.

For example, Japanese Patent Laid-open No. 2010-57831 discloses an aspiration catheter in which a guidewire lumen is integrally disposed on the distal side of an aspiration tube provided therein with an aspiration lumen, and the proximal end of the guidewire lumen is opened into the aspiration lumen. In addition, Japanese Patent Laid-open No. 2006-297063 discloses an aspiration catheter in which a guidewire tube is provided at an outer surface on the distal side of an aspiration tube.

Since an aspiration catheter as above-mentioned is inserted into a living body, its outside diameter should desirably be as small as possible. On the other hand, for assured aspiration of a foreign body, a sufficient flow path area (sectional area) of the aspiration lumen has to be secured. In addition, it is desirable for the aspiration catheter to be high in operationality (to possess good operational properties) such as a property of permitting easy and repeated removal of foreign bodies present at a plurality of parts in a living body, by one-time insertion of the aspiration catheter into the living body.

In the case of the aspiration catheter described in Japanese Patent Laid-open No. 2010-57831, however, the proximal end of the guidewire lumen opens into the aspiration lumen and, therefore, the guidewire has to be once pulled off at the time of aspiration. Therefore, at the time of moving the aspiration catheter distally and/or proximally in a living body for removing the next foreign body after removal of a foreign body, it is necessary to again insert the guidewire, leading to an intricate procedure. In the case of the aspiration catheter described in Japanese Patent Laid-open No. 2006-297063, the proximal opening portion of the guidewire lumen is partly embedded in a slant portion of an outer surface of the aspiration tube. Therefore, the proximal end of the guidewire inserted via the distal opening portion may be caught on the aspiration tube outer surface in the periphery of the proximal opening portion of the guidewire lumen, so that much labor may be needed to insert and pass the guidewire.

SUMMARY

The aspiration catheter disclosed here exhibits high operationality and other desirable characteristics.

According to one aspect, the aspiration catheter includes an aspiration tube and an aspiration lumen extending between and opening to the distal and proximal ends of the aspiration tube, and a guidewire tube bonded to the outer surface of the aspiration tube on a distal end portion of the aspiration tube, with the guidewire tube being parallel to the aspiration tube. A guidewire lumen extends through the guidewire tube and opens at a proximal opening located at a proximal end of the guidewire tube. The outer surface of the aspiration tube has a flat portion where the outer surface is parallel to an axial direction of the aspiration lumen, and the proximal opening of the guidewire lumen is located at the flat portion of the outer surface of the aspiration tube.

The proximal opening portion of the guidewire lumen serving as a leading-out port for the guidewire is located at the flat portion of the aspiration tube. This helps ensure that when the proximal end of the guidewire inserted in the guidewire lumen is led out via the proximal opening portion, the proximal end is prevented from being caught on the outer surface of the aspiration tube. Therefore, trackability of the guidewire in relation to the aspiration tube is enhanced, and, accordingly, operationality of the aspiration catheter is facilitated.

The aspiration lumen is preferably circular in cross-sectional shape in a direction orthogonal to the axial direction at a proximal-side portion at which the guidewire tube and guidewire lumen do not exist, and has a cut-out circular shape obtained by cutting out a part of a circular shape as the cross-sectional shape in a direction orthogonal to the axial direction at a distal-side portion arranged parallel to the guidewire lumen. This makes it possible to secure a sufficient flow path area (sectional area) of the aspiration lumen, while making the outside diameter of the aspiration catheter as small as possible. Consequently, quite smooth aspiration of foreign body can be realized.

The aspiration tube is preferably provided, on the proximal side of a part corresponding to the flat portion, with a proximal-side slant portion increasing in outside diameter toward the proximal side. This helps ensure that the guidewire guided on the flat portion is slid along and in contact with the proximal-side slant portion. Consequently, the guidewire can be passed on the outer surface of the aspiration tube further smoothly. Also, the aspiration tube is preferably provided, on the distal side of a part corresponding to the flat portion, with a distal-side slant portion decreasing in outside diameter toward the distal side. This helps ensure that the guidewire inserted in the guidewire lumen can be led onto the flat portion more smoothly.

The guidewire lumen can be provided, at a position corresponding to the distal-side slant portion, with a slant portion increasing in diameter toward the proximal side. In this way, the guidewire inserted in the guidewire lumen can be smoothly led out to the opening portion, which is opening on the upper side. The flat portion of the aspiration tube can be provided with a groove portion continuous with the proximal opening portion of the guidewire lumen along the axial direction of the aspiration tube. This helps ensure that the guidewire inserted in the guidewire lumen can be guided toward the proximal side more smoothly. In this case, preferably, the groove portion communicates with the guidewire lumen while being gradually slanted from the proximal side toward the distal side of the aspiration tube.

The proximal opening portion of the guidewire lumen is preferably formed obliquely so that the outside diameter of the guidewire tube increases toward the distal side of the guidewire lumen, at the flat portion.

The proximal opening portion of the guidewire lumen serving as the leading-out port for the guidewire is located at the flat portion of the aspiration tube. When the proximal end of the guidewire inserted in the guidewire lumen is led out via the proximal opening portion, the proximal end is inhibited or prevented from being caught on the outer surface of the aspiration tube, whereby trackability of the guidewire in relation to the aspiration tube is enhanced. Consequently, operationality of the aspiration catheter is enhanced.

BRIEF DESCRIPTION OF THE DRAWINGS

FIG. 3A is a cross-sectional view along the section line 3A-3A of FIG. 2A.

DETAILED DESCRIPTION

The detailed description which follows describes the features of one example of the aspiration catheter disclosed here, and also describes a manufacturing method for the aspiration catheter, with reference to the accompanying drawings.

1. Description of General Configuration of Aspiration Catheter

Figure 1:
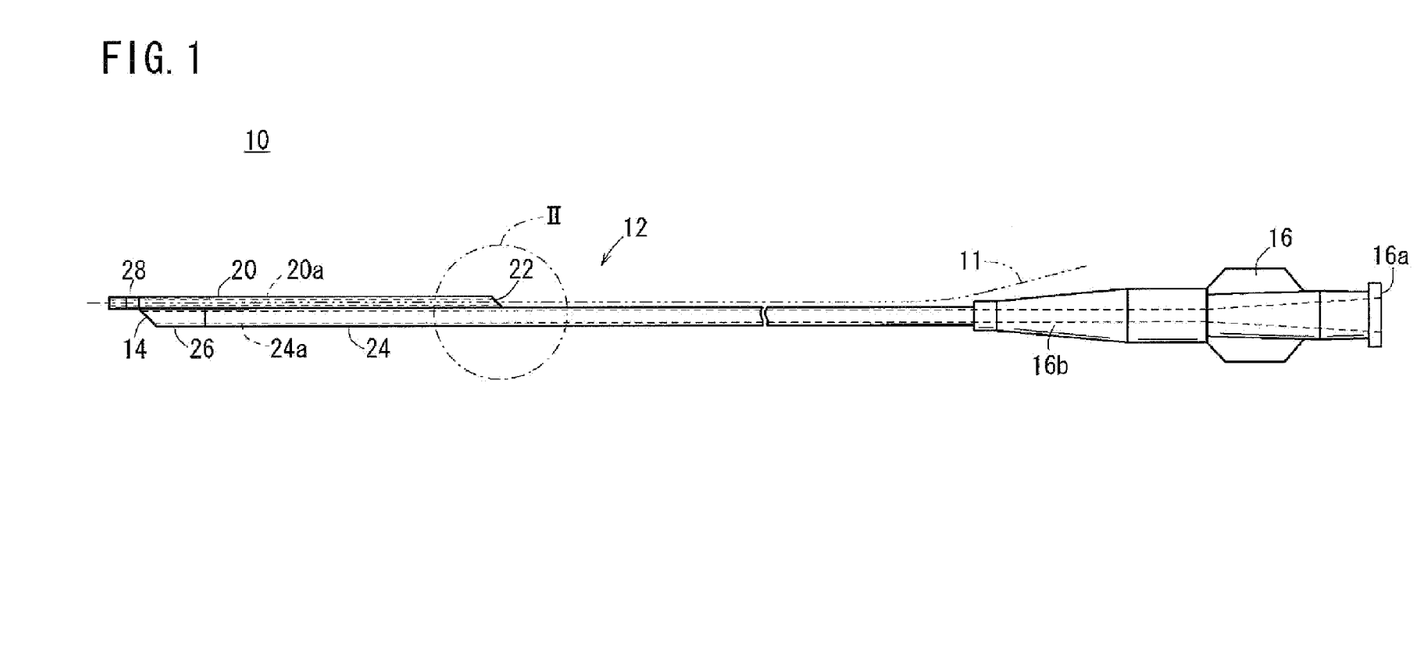
FIG. 1 is a side view of an aspiration catheter according to one embodiment disclosed here.

FIG. 1 generally illustrates the one embodiment of an aspiration catheter 10 disclosed here by way of example. The aspiration catheter 10 according to this embodiment is a medical instrument having a long shaft body 12 which is inserted following a guidewire 11 preceding in the lumen of a guiding catheter (not shown) preliminarily inserted into a living-body organ, and then a foreign body such as a thrombus in a blood vessel is removed by aspiration via a distal aspiration port 14 of the aspiration catheter. The aspiration catheter 10 is used, for example, to remove a thrombus present in a coronary artery, and also has useful application to aspirate a foreign body present in a living-body tubular organ such as, for example, other blood vessels, a bile duct, the trachea, the esophagus, the urethra, and other organs.

As shown in FIG. 1, the aspiration catheter 10 includes the shaft body 12 which is relatively small in diameter and elongated, and a hub 16 connected to the proximal end of the shaft body 12. The shaft body 12 includes a guidewire lumen 20a in the vicinity of the distal end portion of the shaft body 12. In the illustrated embodiment, the guidewire lumen 20a is limited to the distal end portion of the shaft body 12 (i.e., the guidewire lumen 20a does not extend the entire axial extent of the shaft body 12).

Figure 2A:
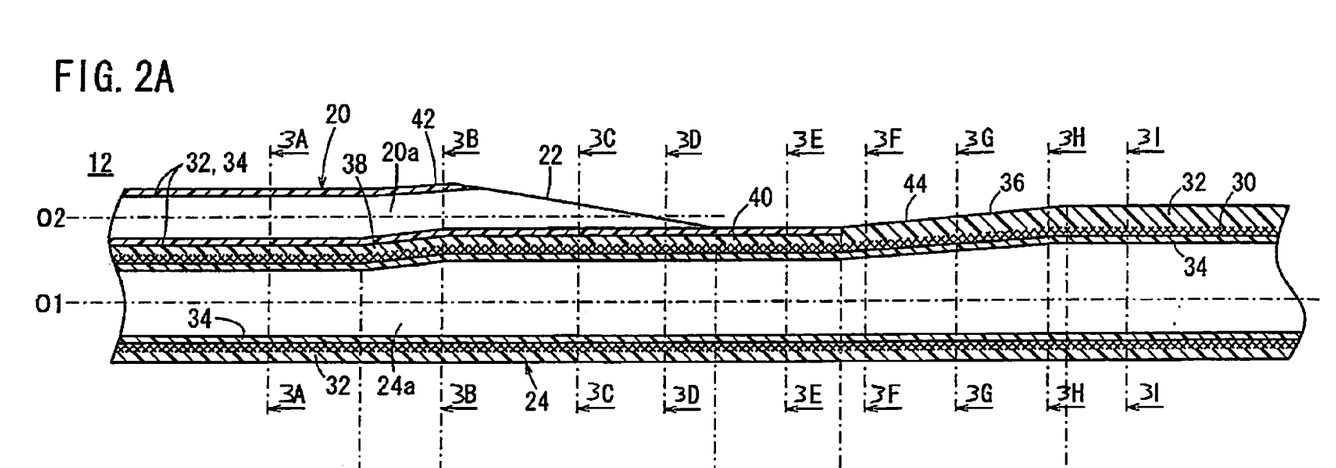
FIG. 2A is a longitudinal cross-sectional view, in an enlarged form, of the part of the catheter indicated by the one-dot chain line circle II in FIG. 1.
Figure 2B:
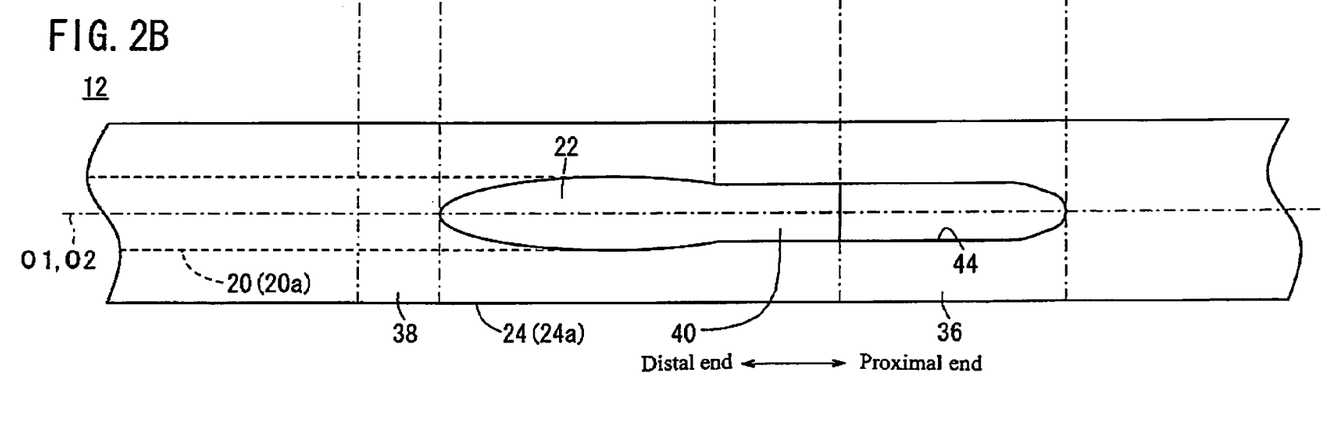
FIG. 2B is a plan view of the shaft body shown in FIG. 2A.
Figure 3B:
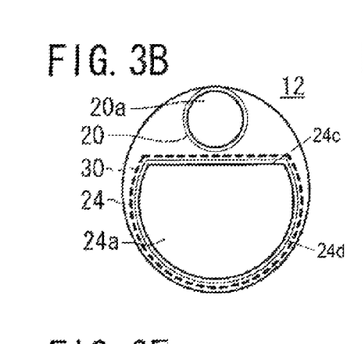
FIG. 3B is a cross-sectional view along the section line 3B-3B of FIG. 2A.
Figure 3C:
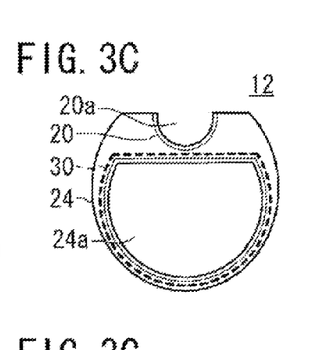
FIG. 3C is a cross-sectional view along the section line 3C-3C of FIG. 2A.
Figure 3D:
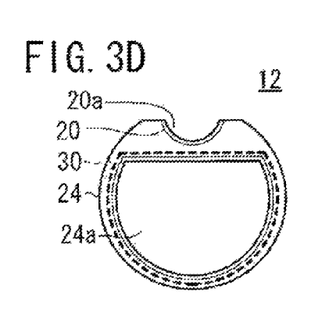
FIG. 3D is a cross-sectional view along the section line 3D-3D of FIG. 2A.
Figure 3E:
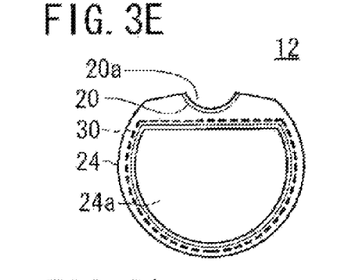
FIG. 3E is a cross-sectional view along the section line 3E-3E of FIG. 2A.
Figure 3F:
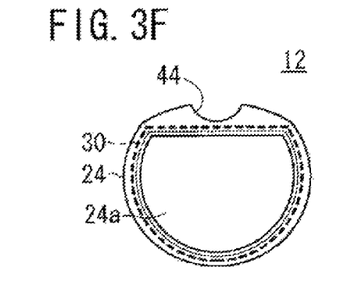
FIG. 3F is a cross-sectional view along the section line 3F-3F of FIG. 2A.
Figure 3G:
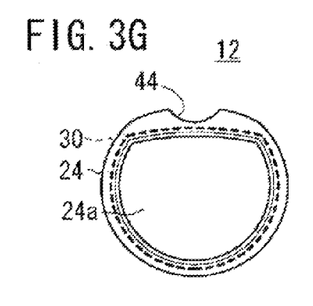
FIG. 3G is a cross-sectional view along the section line 3G-3G of FIG. 2A.
Figure 3H:
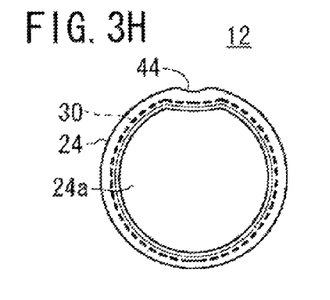
FIG. 3H is a cross-sectional view along the section line H-H of FIG. 2A.
Figure 3I:
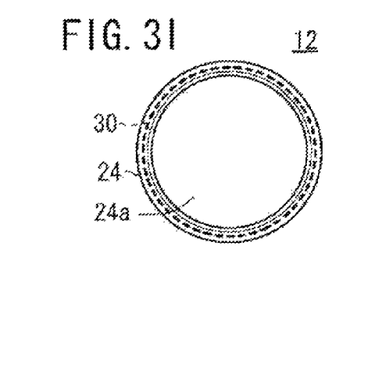
FIG. 3I is a cross-sectional view along the section line 3I-3I of FIG. 2A.

In FIGS. 1 and 2, the right side (the hub 16 side) of the shaft body 12 is referred to as the "proximal" side, and the left side (the aspiration port 14 side) of the shaft body 12 is referred to as the "distal" side. This same nomenclature applies to other figures as well.

The shaft body 12 includes an aspiration tube 24 through which extends an aspiration lumen 24a opening to both the distal end and the proximal end of the aspiration tube 24 to thus communicate the distal end with the proximal end. The shaft body 12 also includes a guidewire tube 20 which is fixed or bonded to the distal-side outer surface of the aspiration tube 24. In the illustrated embodiment, except for the proximal end portion of the guidewire tube 20, the guidewire tube 20 and the aspiration tube 24 are parallel to one another (inclusive of substantially parallel). That is, in the illustrated embodiment, at least the distal half of the guidewire tube 20 is parallel to the aspiration tube 24 (inclusive of substantially parallel). The guidewire lumen 20a passes completely through the guidewire tube 20 from the distal end of the guidewire tube 20 to the proximal end of the guidewire tube 20 so that the guidewire lumen 20a opens to both the distal end and the proximal end of the guidewire tube 20. The aspiration tube 24 and the guidewire tube 20 do not communicate with each other, but are positioned adjacent to and independent from each other.

A distal tip 26 is provided at the most distal end of the aspiration tube 24, and the distal tip 26 includes the aspiration port 14 which opens to an inclined surface at the distal end of the distal tip 26. The most distal end of the guidewire tube 20 constitutes a protruding part that protrudes a little beyond the distal most end of the aspiration port 14, and a radiopaque marker (contrast marker) 28 is firmly attached to this protruding part. The radiopaque marker 28 is provided at an outer peripheral surface of the guidewire tube 20, and is formed from a radiopaque material such as, for example, gold or platinum so that the distal end position of the aspiration catheter in a living body can be visually checked or confirmed under radioscopy. The radiopaque marker 28 may be exposed or may be embedded in the guidewire tube 20, without being exposed at the outer peripheral surface.

The aspiration tube 24 has its proximal end connected to and in communication with the hub 16. A negative pressure supply device such as a syringe can be connected to the negative pressure supply device via, for example, a luer taper 16a on the hub 16. By virtue of the negative pressure generated in the negative pressure supply device, a foreign body such as thrombus can be aspirated through the aspiration port 14 and transferred through the aspiration lumen 24a, to be removed to the exterior. The distal end of the hub 16 is a strain relief section 16b that prevents the aspiration tube 24 from bending (kinking) at the connection portion between the aspiration tube 24 and the hub 16.

As shown in FIG. 2A, a braid 30 is embedded in the aspiration tube 24 and forms a reinforcement member. The braid 30 extends along a peripheral edge portion of the aspiration lumen 24a from the distal end to the proximal end of the aspiration lumen 24a. The braid 30 can be in the form of a coil or a mesh structure formed from a metal such as stainless steel. In other words, the aspiration tube 24 is a braided tube which is reinforced by embedding the braid 30 in the wall surface. The aspiration tube 24 may be so configured that the braid 30 is absent at the distal tip 26.

The guidewire tube 20 is so configured that the guidewire 11 introduced therein via the distal opening of the guidewire lumen 20a (guidewire tube 20) can pass through the guidewire lumen 20a and can be led out to the exterior via an opening portion (proximal opening) 22 at the proximal end of the guidewire lumen 20a (guidewire tube 20). The bonding or fixing structure between the guidewire tube 20 and the aspiration tube 24, and the peripheral structure of the opening portion 22, will be described in more detail later.

The aspiration tube 24 is, for example, a flexible tube which has an outside diameter of about 1.1 to 4.0 mm, preferably about 1.2 to 3.0 mm, a material thickness of about 20 to 500 μm, preferably about 100 to 400 μm, and a length of about 500 to 2000 mm, preferably 1200 to 1600 mm. The guidewire tube 20 is, for example, a flexible tube which has an outside diameter of about 0.4 to 1.2 mm, preferably about 0.6 to 1.0 mm, a material thickness of about 10 to 400 μm, preferably about 100 to 250 μm, and a length of about 10 to 350 mm, preferably about 25 to 250 mm.

The aspiration tube 24 and the guidewire tube 20 are preferably configured to exhibit appropriate flexibility and appropriate strength (springiness, rigidity), for example a structure that increases stepwise or gradually in rigidity from the distal side toward the proximal side, in order that the elongated shaft body 12 can be relatively smoothly inserted into, for example, a guiding catheter or a blood vessel while the user grips and operates the proximal side of the shaft body 12. In addition, the aspiration lumen 24a and the guidewire lumen 20a, as inner cavities of the aspiration tube 24 and the guidewire tube 20 respectively, are preferably so configured that a foreign body and the guidewire 11 can be relatively smoothly passed therethrough.

In view of this, the aspiration tube 24 and the guidewire tube 20 are preferably composed of a two-layer tube having, for example, an outer layer 32 of a polyamide elastomer and an inner layer 34 of PFA (tetrafluoroethylene-perfluoroalkoxyethylene copolymer) (see FIG. 2A). In addition, since the aspiration tube 24 has a sufficient length as above-mentioned, the aspiration tube 24 is preferably so configured that, for example, a predetermined length portion from the distal end is formed of a flexible material or structure, and the proximal side of the aspiration tube 24 is formed of a material or structure of a little higher or greater rigidity. The distal tip 26 may be formed of a material similar to that of the aspiration tube 24, and is preferably higher in rigidity than the aspiration tube 24, in order to secure assured removal of foreign body and passability in a living body.

2. Description of Bond Structure Between the Aspiration Tube 24 and the Guidewire Tube 20, and the Peripheral Structure of the Opening Portion 22

The bond structure between the aspiration tube 24 and the guidewire tube 20, and the peripheral structure of the opening portion 22, are discussed below with reference to FIGS. 3A-3I. In FIGS. 3A-3I, cross-hatching indicative of cross-section is omitted, for simplicity of drawing.

As shown in FIG. 2A, the aspiration tube 24 is configured so that a proximal-side slant (inclined) portion 36 and a distal-side slant (inclined) portion 38 are provided on the upper surface side of the aspiration tube 24 in FIG. 2A, namely on the outer surface on the side of the aspiration tube 24 bonded to the guidewire tube 20. The aspiration tube 24 also includes a flat portion 40 parallel (inclusive of substantially parallel) to the axis O1 of the aspiration lumen 24a in side view shown in FIG. 2A. The flat portion 40 is also parallel (inclusive of substantially parallel) to the axis O2 of the guidewire lumen 20a in the side view shown in FIG. 2A. The flat portion 40 is positioned between the proximal-side slant portion 36 and the distal-side slant portion 38. In the illustrated embodiment, the proximal-most end of the flat portion 40 is directly connected to the distal-most end of the proximal-side slanting portion 36, and the distal-most end of the flat portion 40 is directly connected to the proximal-most end of the distal-side slanting portion 38.

The flat portion 40 is shaped as if a part of the aspiration tube 24 which is circular in outside diameter section was externally collapsed flat. The flat portion 40 is thus an outside surface flat portion 24c (circumferential portion), meaning the outside surface of the aspiration tube 24 is flat. The outside surface flat portion thus represents a circumferential part 24c (circumferential portion) of the outer surface (i.e., not the entire outer surface) which is not curved and which does not possess the same radius of curvature as the circumferential portion 24d of the outer surface which is cylindrically shaped. Stated differently, the outside surface flat portion represents a circumferential part of the outer surface which does not possess the same radius of curvature as the remainder of the outer circumference. At the inner surface of the aspiration lumen 24a corresponding to the flat portion 40, an inner cavity flat portion is present as shown in FIG. 2A. The braid 30 present between the outside surface flat portion 40 and the inner cavity flat portion is also flat (inclusive of substantially flat).

The proximal-side slant portion 36 on the proximal side is continuous with the flat portion 40 and is so shaped that its outer surface (outside diameter) increases in outer diameter toward the proximal side, whereas the distal-side slant portion 38 on the distal side is continuous with the flat portion 40 and is so shaped that its outer surface (outside diameter) decreases in outer diameter toward the distal side. In other words, the proximal-side slant portion 36, the distal-side slant portion 38 and the flat portion 40 are formed continuously in the axial direction on the same circumferential direction of the aspiration tube 24, meaning the portions abut one another as illustrated and the three portions are positioned immediately axially adjacent one another without other intervening portions. The inner surface of the aspiration lumen 24a in the proximal-side slant portion 36 and the inner surface of the aspiration lumen 24a in the distal-side slant portion 38 are slanted or inclined at the same angle (inclusive of substantially the same angle). These slant portions 36, 38 are so configured that the area of the flat portion 40 of the outer surface is varied, specifically, enlarged or reduced, meaning that the area of the two slant portions 36, 38 and the flat portion 40 could be independently determined or could be independent of one another. In the illustrated embodiment, the circumferential width of each of the slant portions 36, 38 and the flat portion 40 of the outer surface are almost the same, but the longitudinal length could vary so that each portion can have a greater or smaller area.

As shown in FIG. 2A, while the flat portion 40 is parallel to the axis O1 (O2) in side view, the proximal-side slant portion 36 and the distal-side slant portion 38 are configured so that imaginary continuations of these slant surfaces intersect the axis O1 (O2) in side view. The flat portion 40 is not limited to the configuration in which it is perfectly parallel to the axis O1 (O2) in side view, and a configuration may be adopted in which the flat portion 40 is a little slanted or inclined relative to the axis O1 (O2) so as to be substantially parallel or is recessed and projected and substantially parallel to the axis O1 (O2). In other words, the flat portion 40 can include portions configured so that an imaginary continuation of such portions intersect the axis O1 at an intersection angle smaller than the intersection angles at which the imaginary continuations of the proximal-side slant portion 36 and the distal-side slant portion 38, present on the proximal-side and the distal-side of the flat portion 40, intersect the axis O1.

Thus, along the direction from the distal side toward the proximal side, the aspiration tube 24 has a two-stage diameter-increasing slanted shape in which it increases in outside diameter at the distal-side slant portion 38, and, after extending through the flat portion 40, it again increases in outside diameter at the proximal-side slant portion 36 (see also FIGS. 3A-3I). To be more specific, at the proximal-side slant portion 36, the inside diameter (inside area) of the aspiration lumen 24a varies so as to become greater than the inside diameter of the flat portion 40, and, at the distal-side slant portion 38, the inside diameter (inside area) of the aspiration lumen 24a varies so as to become smaller than the inside diameter of the flat portion 40. A distal-side flat portion is present on the distal side of the distal-side slant portion 38. The distal-side flat portion is shaped as if a part of the aspiration tube 24 being circular in outside diameter section were externally collapsed flat. The distal-side flat portion is thus an outside surface distal-side flat portion 24c (circumferential portion) because the outside surface of this portion 24c of the aspiration tube 24 is flat. The outside surface distal-side flat portion thus represents a part of the outer surface (i.e., not the entire outer surface) which is not curved. Stated differently, the outside surface distal-side flat portion represents a circumferential part 24c (circumferential portion) of the outer surface which does not possess the same radius of curvature as the remainder 24d of the circumference. The inner surface of the aspiration lumen 24a at the distal-side flat portion includes a distal-side inner cavity flat portion. The braid 30 present between the outside surface distal-side flat portion and the distal-side inner cavity flat portion is also flat (inclusive of substantially flat).

Specifically, the aspiration lumen 24a is so formed that the cross-sectional shape, in a direction orthogonal to the axis O1, of a distal-side portion parallel to the guidewire lumen 20a is a circular shape with a non-circular part obtained by providing a cutout in a part of the circular shape (more specifically, an irregular shape or a shape obtained by cutting out or removing a part of a circle along a horizontal direction parallel to a diameter) (see FIGS. 3A-3E). In other words, the cross-sectional shape of the aspiration lumen 24a is a circle, but with a circumferential part of the curved surface of the circle removed and replaced by a non-circular circumferential part. Further, the aspiration lumen 24a is so formed that the cross-sectional shape, in a direction orthogonal to the axis O1, of a portion on the proximal side relative to the proximal-side slant portion 36 (a portion where the guidewire tube 20 is absent) is a circular shape (see FIG. 3I), and a portion between this portion and the proximal-side slant portion 36 is a transition portion where the cutout in the circular shape is gradually decreased from the distal side toward the proximal side (see FIGS. 3F-3H). The outer layer 32 of the aspiration lumen 24a at the portion having the cut-out circular shape (irregular shape) may vary in hardness along the direction of the axis O1. For example, the outer layer 32 at the most distal portion is preferably harder than the outer layer 32 at a portion immediately on the proximal side of the most distal portion.

The proximal opening 22 of the guidewire tube 20 has an end face inclined so that an imaginary continuation of the inclined end face intersects the axis O1. The guidewire tube 20 is so formed that substantially the whole part of the proximal opening 22 at its proximal end is located at the flat portion 40 (i.e., the entire proximal opening 22 at the inclined end face axially overlaps the flat portion 40), and its distal end is set at a position a little protruding from the distal tip 26. That is, the distal tip of the guidewire tube 20 protrudes distally beyond the distal tip 26. In this condition, the whole part in the axial direction of the guidewire tube 20 is integrally bonded to an outer surface (upper surface) of the aspiration tube 24 by, for example, heat welding.

As shown in FIGS. 2A and 2B, the guidewire tube 20 is provided, at a position close to an upper end portion of the opening portion 22, with a slant portion 42 which corresponds to (axially overlaps, in plan view, with) the distal-side slant portion 38. In short, the guidewire lumen 20a is so formed that the portion of the guidewire lumen 20a ranging from the distal opening to the distal side of the slant portion 42 is a rectilinear (inclusive of substantially rectilinear) passage, and proceeding further proximally the guidewire lumen 20a is then oriented or inclined a little upward (outward) at the slant portion 42, and it is opening at the opening portion 22. In other words, the aspiration catheter 10 has a maximum outside diameter at a position of transition from the tubular shape on the most proximal side of the guidewire tube 20 to the opening portion (inclined opening portion) 22. The maximum outer diameter of the aspiration catheter 24 is just to the right of the section line 3B-3B in FIG. 2A. The guidewire lumen can be formed with a constant diameter core wire (as described below) and so the diameter of the guidewire lumen is generally the same regardless of the position along the length of the guidewire lumen.

As shown in FIGS. 3A-3I, the aspiration tube 24 is provided, in its outer surface (upper surface which is the portion of the outer surface which faces upward when the catheter is oriented in the manner shown in FIGS. 3A-3I) with a recessed groove portion 44. The recessed groove portion 44 extends from the flat portion 40 which faces the proximal opening 22 of the guidewire lumen 20a to the proximal end of the proximal-side slant portion 36. The recessed groove portion 44 extends continuously from the proximal end of the proximal-side slant portion 36 to the proximal end of the guidewire lumen 20a (the opening portion 22) as shown in FIG. 2a. The groove portion 44 becomes deeper by virtue of the recessed groove portion 44 being inclined so as to gradually decrease in diameter from the proximal side toward the distal side of the aspiration tube 24, and communicates with the guidewire lumen 20a. In FIG. 2A, for simplicity, only a bottom surface of the groove portion 44 is shown, and the wall portions rising from the bottom surface are omitted.

With respect to the cross-section in a direction orthogonal to the axis O1 (O2) at positions 3A-3A thru 3I-3I in FIG. 2A, the minor diameter of the aspiration lumen 24a is referred to as a, its major diameter as b, the major outer diameter of the shaft body 12 is referred to as c, its minor outer diameter as d, and the diameter of the guidewire lumen 20a is referred to as e, as shown in FIG. 3A. As for the sizes of the minor diameter a, the major diameter b, the major outer diameter c, the minor outer diameter d and the diameter e, for example, a configuration may be adopted in which the minor diameter a is 0.92 mm, the major diameter b is 1.12 mm, the major outer diameter c is 1.56 mm, the minor outer diameter d is 1.31 mm, and the diameter e is 0.40 mm; naturally, these sizes may be appropriately changed according to the specifications of the aspiration catheter 10, and so on. The minor diameter a of the aspiration lumen 24a is preferably not less than two times the diameter e of the guidewire lumen 20a.

In this case, the ratio (a/b) of the minor diameter a to the major diameter b of the aspiration lumen 24a and the ratio (d/c) of the minor outer diameter d to the major outer diameter c of the shaft body 12 at a portion where the guidewire tube 20 is bonded to the aspiration tube 24, a configuration is adopted in which, for example, the ratio (a/b) is about 0.821, and the ratio (d/c) is about 0.840, both ratios thus being comparable to each other. In other words, a configuration may be adopted in which both the ratio (a/b) and the ratio (d/c) are not less than 0.8, and, further, both of them are comparable to each other, for example, they are mutually in the range of about ±20%, preferably about ±10% (meaning one is not greater or smaller than the other by more than 20%, and preferably one is not greater or smaller than the other by more than 10%). This configuration helps ensure that the cross-sectional shape in a direction orthogonal to the axis O1 of the shaft body 12 at the portion where the guidewire tube 20 is bonded to the aspiration tube 24 possesses a shape that is close to a circular shape. As a result, an operation of inserting and passing the aspiration catheter 10 through the guiding catheter is facilitated.

3. Description of Operation of Aspiration Catheter

Now, an operation of the aspiration catheter 10 configured as above is described.

First, the aspiration catheter 10 can be used in a manner similar to general aspiration catheters. Specifically, a guiding catheter is set indwelling at a target position in a coronary artery, and the guidewire 11 (shown in FIG. 1) is inserted into and passed through the guiding catheter. Subsequently, the guidewire 11 is passed from the distal end to the proximal opening 22 of the guidewire lumen 20a, whereby the distal end of the shaft body 12 is able to reach the target position. Then, a negative pressure supply device such as a syringe is connected to the hub 16, and a negative pressure is generated inside the aspiration lumen 24a, whereby a foreign body such as thrombus is aspirated via the distal aspiration port 14, to be removed through the aspiration lumen 24a to the exterior of the living body.

In this case, in the aspiration catheter 10, the proximal opening 22 serving as the lead-out port (outlet) of the guidewire 11 is circumferentially aligned with the flat portion 40 of the aspiration tube 24 so that the proximal opening 22 is located at the flat portion 40 of the aspiration tube 24. Therefore, with the guidewire 11 inserted and passed through the guidewire lumen 20a, the proximal end is inhibited or prevented from being caught on the outer surface of the aspiration tube 24 when led out via the opening portion 22, so that trackability of the guidewire 11 in relation to the aspiration tube 24 (the shaft body 12) is enhanced. Accordingly, the aspiration catheter 10 can be relatively smoothly inserted into the living body, and operationality of the aspiration catheter 10 can be enhanced.

Moreover, since the guidewire lumen 20a is provided independently of the aspiration lumen 24a, aspiration can be performed with the guidewire 11 kept inserted. Therefore, after a predetermined foreign body in a blood vessel is removed by aspiration and when another foreign body present on the distal or proximal side of the blood vessel is to be removed by aspiration, the shaft body 12 can be moved distally and proximally by utilizing directly the guidewire 11 inserted in the guidewire lumen 20a, so that the intended procedure can be carried out relatively easily and speedily. On the other hand, in the case where foreign bodies to be removed in succession are different in shape or in the case of removing a foreign body by again moving the aspiration catheter 10 into another blood vessel, it may be necessary to once pull off the aspiration catheter 10. In this case, in the present aspiration catheter 10, the provision of the flat portion 40 as abovementioned helps ensures smooth insertion and passage of the guidewire 11, so that re-insertion and so on of the aspiration catheter operations can be performed quite easily.

As above-mentioned, the aspiration lumen 24a has a cutout circular cross-sectional shape in which a cutout exists at a part of its distal-side portion and arranged to be parallel to the guidewire lumen 20a, and has a circular cross-sectional shape (inclusive of substantially circular) at its proximal-side portion at which the guidewire tube 20 and guidewire lumen 20a do not exist. Therefore, as understood from FIGS. 3A-3I, the flow path area (sectional area) of the aspiration lumen 24a can be sufficiently secured, while forming the aspiration catheter 10 as small as possible in outside diameter, whereby smooth aspiration of foreign body can be realized.

The groove portion 44 which is continuous with the proximal opening 22 of the guidewire lumen 20a is formed in the outer surface of the aspiration tube 24, specifically, at a position corresponding to the flat portion 40 and the proximal-side slant portion 36. This helps ensure that the smooth insertion and passage of the guidewire 11 due to the presence of the flat portion 40 as above-mentioned can be further improved, and operationality of the aspiration catheter 10 is further enhanced.

Because the proximal-side slant portion 36 is provided on the proximal side and in continuity with the flat portion 40, the guidewire 11 guided by the groove portion 44 on the flat portion 40 is slid in contact with the proximal-side slant portion 36. Therefore, the guidewire 11 can be passed more smoothly along the outer surface of the aspiration tube 24. In addition, because the distal-side slant portion 38 is provided on the distal side of the flat portion 40, the guidewire 11 inserted in the guidewire lumen 20a can be guided onto the flat portion 40 further smoothly. Further, the guidewire lumen 20a has the slant portion 42 at a position corresponding to the distal-side slant portion 38. This helps ensure that the guidewire 11 inserted in the guidewire lumen 20a can be more smoothly guided out to the opening portion 22, which is an inclined cut surface opening on the upper side.

Figure 4B:
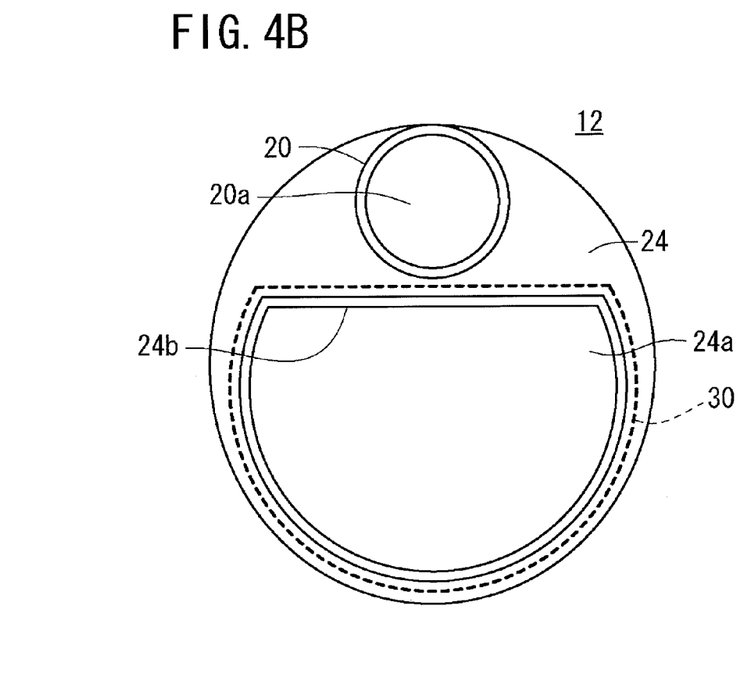
FIG. 4B is a cross-sectional view of a shaft body formed by the second core rod shown in FIG. 4A.
Figure 5A:
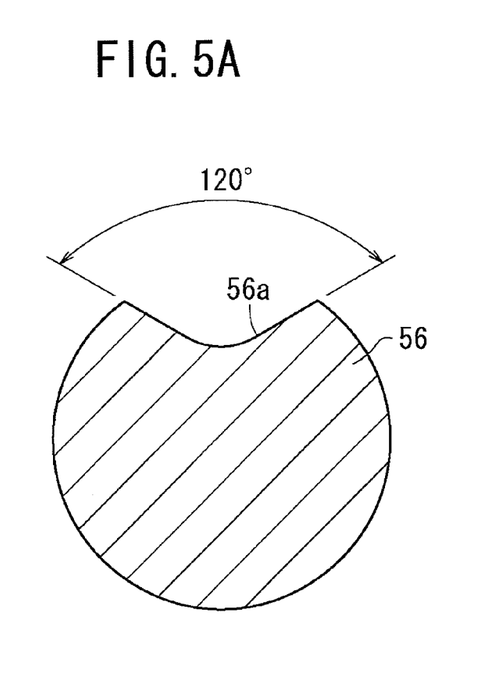
FIG. 5A is a cross-sectional view showing a modification of the second core rod.
Figure 5B:
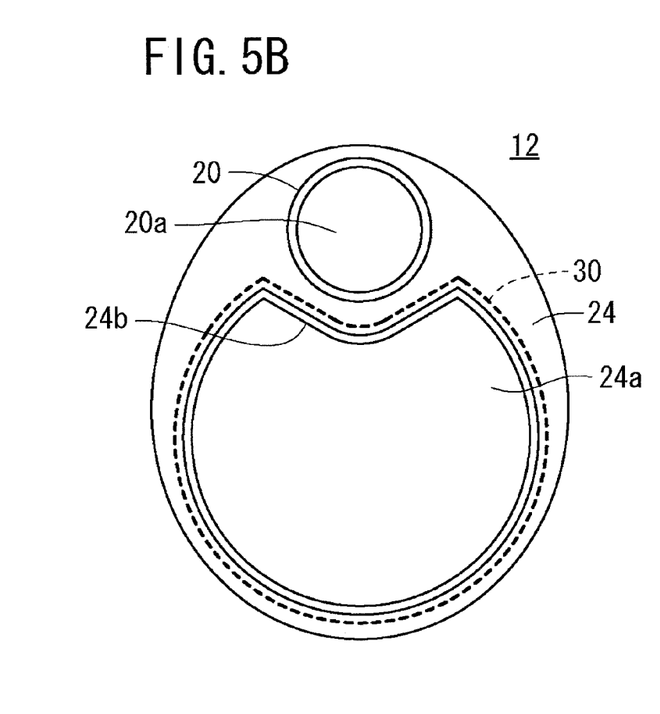
FIG. 5B is a cross-sectional view of a shaft body formed by the second core rod shown in FIG. 5A.
Figure 6A:
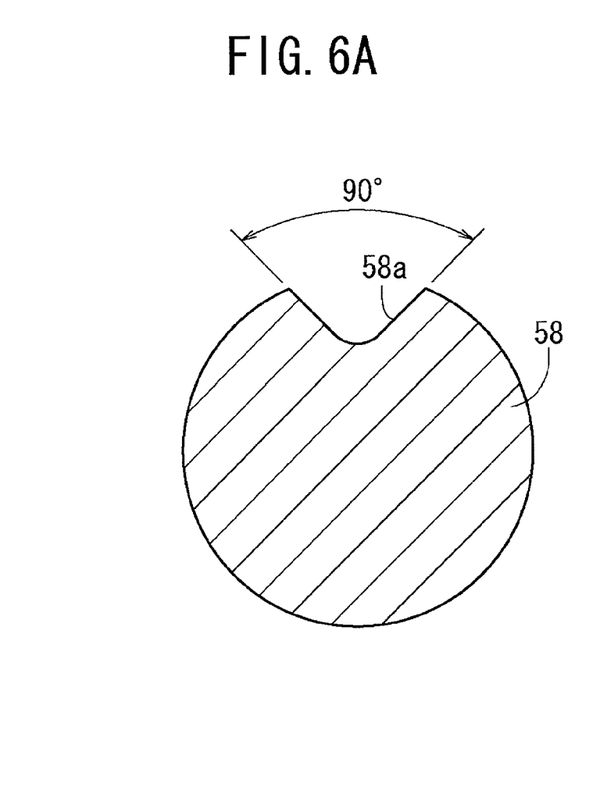
FIG. 6A is a cross-sectional view showing another modification of the second core rod.
Figure 6B:
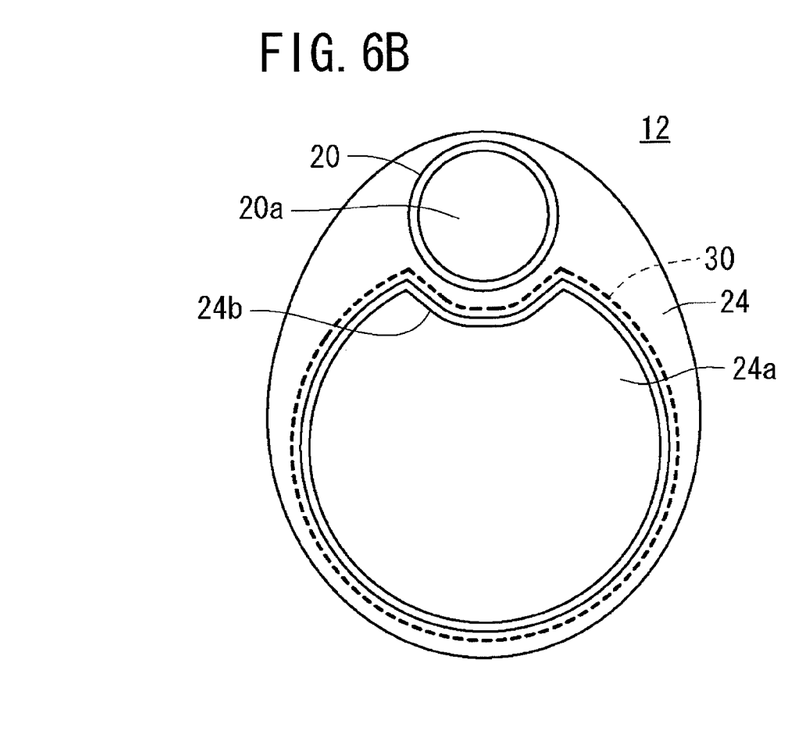
FIG. 6B is a cross-sectional view of a shaft body formed by the second core rod shown in FIG. 6A.

The cross-sectional shape of the aspiration tube 24 (the aspiration lumen 24a) at the part where the guidewire tube 20 and the aspiration tube 24 are arranged in parallel to each other as shown in FIG. 3A may be so configured that a recess 24b having a roughly V-shaped form shown in FIG. 5B or a roughly U-shaped form shown in FIG. 6B is provided, and the braid 30 may be so configured that it is embedded along the whole perimeter of an edge portion of the aspiration lumen 24a inclusive of the recess 24b. This helps ensure that the flow path area (sectional area) of the aspiration lumen 24a can be further increased, while reducing the outside diameter of the aspiration catheter 10. Naturally, the cross-sectional shape of the aspiration tube 24 (the aspiration lumen 24a) is not limited to the shapes shown as examples in FIGS. 4B, 5B and 6B; thus, various sectional shapes can be adopted.

4. Description of Method of Manufacturing Aspiration Catheter

Now, an example of a method of manufacturing the aspiration catheter 10 as above is described.

Figure 4A:
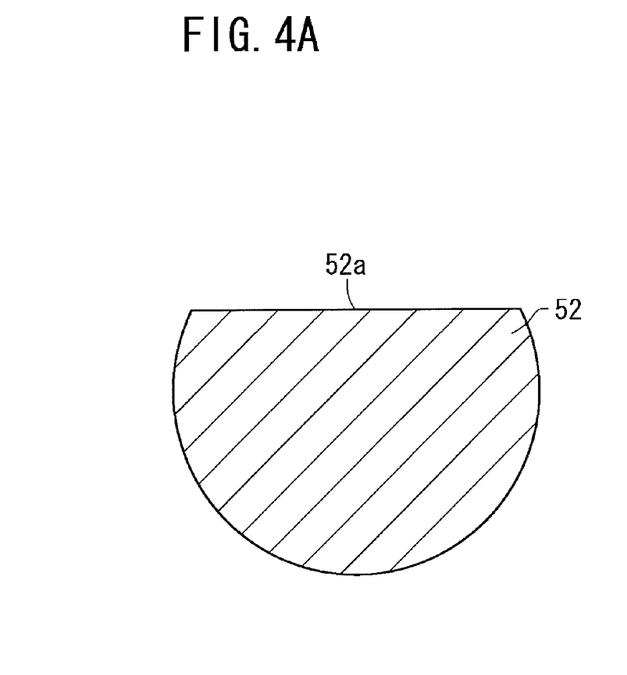
FIG. 4A is a cross-sectional view of a second core rod.

First, a first core rod is inserted into a guidewire lumen 20a of a guidewire tube 20 prepared as a tube blank set to a predetermined length, and a second core rod 52 is inserted into an aspiration lumen 24a of an aspiration tube 24 prepared as a tube blank set to a predetermined length (see FIG. 4A). The first core rod and the second core rod 52 are formed from a metal such as stainless steel.

Here, the cross-sectional shape in a direction orthogonal to the axial direction of the first core rod is a substantially circular shape over the whole length of the first core rod, whereas the cross-sectional shape in a direction orthogonal to the axial direction of the second core rod 52 is a cut-out circular shape provided with a cutout portion 52a by cutting a part of a circular shape parallel to a diameter, over the whole length of the second core rod 52. In this case, the length of the first core rod is preferably so set that the distal end of the first core rod protrudes a little from the distal opening portion of the guidewire tube 20 and so that the proximal end of the first core rod reaches the proximal end of a proximal-side slant portion 36 of the aspiration tube 24 via an opening portion 22. The length of the second core rod 52 is preferably so set that the distal end of the second core rod 52 protrudes a little from an aspiration port 14 of the aspiration tube 24 and so that the proximal end of the second core rod 52 reaches the position 3I-3I in FIG. 2A.

Next, the guidewire tube 20 with the first core rod inserted therein is disposed parallel to the circumferential position on the outer surface of the aspiration tube 24 with the second core rod 52 inserted therein which corresponds to the cutout portion 52a (see FIG. 4A) of the second core rod 52, and both the tubes are bonded to each other by compression. Therefore, under the pressure exerted from the guidewire tube 20, the aspiration tube 24 (the aspiration lumen 24a) is formed into a shape substantially coinciding with the sectional shape of the second core rod 52.

According to the manufacturing method as above, the first core rod having the substantially circular sectional shape is inserted in the guidewire tube 20, the second core rod 52 having the cut-out circular shape is inserted in the aspiration tube 24, and both the tubes are bonded to each other, whereby the guidewire tube 20 is formed under pressure toward the aspiration tube 24 side by the first core rod. In this case, because the second core rod 52 is provided with the cutout portion 52a, the guidewire tube 20 presses and deforms the aspiration tube 24, and is appropriately embedded into the cutout portion 52a of the second core rod 52, resulting in formation of a shaft body 12 which has one of the cross-sectional shapes shown in FIGS. 2A and 3A-3I.

Therefore, while the aspiration catheter 10 has a structure in which the guidewire lumen 20a is formed independently from the aspiration lumen 24a, the outside diameter of the aspiration catheter 10 can be reduced as much as possible. Moreover, as understood from FIG. 3A, the aspiration lumen 24a is formed in the cut-out circular shape ranging throughout most of the shaft body, other than the region occupied by the guidewire lumen 20a, of the cross-section of the shaft body 12. Accordingly, the flow path area of the aspiration lumen 24a can be increased as much as possible.

Here, in the tube blank constituting the aspiration tube 24, a braid 30 is preliminarily embedded so as to extend along an edge portion of the aspiration lumen 24a from the distal end to the proximal end in the axial direction. At position A in FIG. 2A, the braid 30 is deformed along the shape of the cutout portion 30 of the second core rod 52, so that the guidewire tube 20 is disposed in the state of being appropriately embedded in the deformation-derived space. Consequently, the outside diameter of the aspiration catheter 10 can be reduced as much as possible.

Incidentally, the second core rod 52 for forming the aspiration lumen 24a may be other than the rod material having a roughly semicircular sectional shape shown in FIG. 4A. For example, use can be made of second core rods 56, 58 provided with roughly a 120° or 90° V-shaped or U-shaped cutout portion 56a, 58a on the side on which the guidewire tube 20 is disposed, as shown in FIGS. 5A and 6A.

Consequently, as shown in FIGS. 5B and 6B, in a bonding step in the manufacturing method as above, the guidewire tube 20 (the first core rod) is embedded in a molded manner in the cutout portion 56a, 58a. Therefore, at a position corresponding to position A in FIG. 2A and so on, the cross-sectional shape (inner surface shape) of the aspiration lumen 24a substantially coincides with the cross-sectional shape of the second core rod 56, 58, to give a shape provided with a recess 24b, 24b, and the braid 30 is embedded along the whole perimeter of an edge portion of the aspiration lumen 24a inclusive of the recess 24b (see FIGS. 5B and 6B). Accordingly, the flow path area (cross-sectional area) of the aspiration lumen 24a can be further increased, while reducing the outside diameter of the aspiration catheter 10. Naturally, the shape of the cutout portion of the second core rod is not limited to those shown by way of example as cutout portions 52a, 56a, 58a, and may be shapes and so on in other angular ranges.

As shown in FIGS. 4B, 5B and 6B, the braid 30 is desirably deformed securely at the time of molding so as to coincide with the shape of the cutout portion 52a, 56a, 58a of the second core rod 52, 56, 58 (in the case of the configurations shown by way of example in FIGS. 5B and 6B, finally the shape of the recess 24b). For this purpose, that portion of the aspiration tube 24 to which the guidewire tube 20 is bonded (for example, the portion from the distal end to position A or position B in FIG. 2A) is preferably so configured that the strength (rigidity) of the braid 30 at this portion is set lower than the strength (rigidity) of the proximal-side portion (for example, a portion on the proximal side relative to position I in FIG. 2A). This helps ensure that, at the time of making the shape of the aspiration tube 24 coincident with the shape of the cutout portion 52a, 56a, 58a, the braid 30 can also be deformed relatively smoothly and easily, whereby the productivity and yield of the aspiration catheter 10 are enhanced.

EXAMPLES

Now, an Example of an aspiration catheter 10 constructed in accordance with the disclosure here for purposes of performance evaluation is described, together with a comparison to a Comparative Example.

1. Manufacture of Example of Aspiration Catheter 10

An aspiration tube 24 was produced as follows. A tube including an outer layer 32 formed of a polyamide elastomer, an inner layer 34 formed of a fluororesin, and a round-wire braid reinforcement layer (braid 30) disposed between these layers was used, and was set to have a whole length of 1400 mm, an outside diameter of 1.40 mm, and an inside diameter of 1.10 mm. A guidewire tube 20 was produced as follows. A tube including an outer layer 32 formed of a polyamide elastomer and an inner layer 34 formed of a fluororesin was used, and was set to have an overall length of 90 mm, an outside diameter of 0.64 mm, and an inside diameter of 0.45 mm.

With respect to the aspiration tube 24, a part of the surface of the outer layer 32 was ground away in a circular circumferential shape, from the most distal portion to a portion 1.5 mm distant therefrom toward the proximal side. Then, a distal tip 26 was fitted to overlap with or overlie the part where the surface of the outer layer 32 had been ground away. The distal tip 26 had a length of 30 mm, an outside diameter of 1.40 mm, and an inside diameter of 1.15 mm. Next, a core rod having a diameter of 1.05 mm was inserted into an aspiration lumen 24a, a heat-shrinkable tube was put on so as to overlap with the boundary portion between the aspiration tube 24 and the distal tip 26, and the assembly with the heat-shrinkable tube put on was heated, to bond the aspiration tube 24 and the distal tip 26 to each other. After the heating, the heat-shrinkable tube was removed.

Into a guidewire lumen 20a of the guidewire tube 20, a first core rod circular in sectional shape in a direction orthogonal to the axial direction of the guidewire lumen 20a was inserted so as to protrude from a proximal opening. Besides, into the aspiration lumen 24a of the aspiration tube 24, a second core rod 52 having a roughly cut-out circular shape with a minor diameter a of 0.85 mm and a major diameter b of 1.08 mm (see FIGS. 3A-3E) in sectional shape in a direction orthogonal to the axial direction of the aspiration lumen 24a was inserted to a position about 200 mm distant from the distal side of the aspiration tube 24.

The guidewire tube 20 was disposed on the surface of the outer layer 32 of the aspiration tube 24 coinciding with the position of a cutout portion 52a of the second core rod 52 on the distal side of the aspiration tube 24 (specifically, on a surface faced by the cutout portion 52a). Next, a heat-shrinkable tube was put over the whole body of the guidewire tube 20 and the aspiration tube 24, and the heat-shrinkable tube was heated from the distal end toward the proximal end, whereby the guidewire tube 20 and the aspiration tube 24 was welded to each other. After the heating, the heat-shrinkable tube was removed.

Thereafter, the first core rod was removed from the guidewire tube 20, the second core rod 52 was removed from the aspiration tube 24, and the distal end of the distal tip 26 was cut so as to obtain a predetermined opening shape. In addition, from the position 7 mm distant toward the distal side from the proximal opening portion of the guidewire tube 20, the guidewire tube 20 was cut so as to obtain an inclined opening portion 22. Further, a hub 16 was connected to the proximal end of the tube (aspiration tube 24), to produce the aspiration catheter 10.

The aspiration catheter 10 thus manufactured was substantially circular in outside diameter (cross-sectional shape) with the parallel arrangement of the aspiration tube 24 and the guidewire tube 20 on the distal side, and the substantially circular shape was substantially free of eccentricity. The guidewire lumen 20a of the guidewire tube 20 did not communicate with the aspiration lumen 24a. The cross-section of the aspiration lumen 24a was formed to be a cut-out circular shape, continuously from the distal end of the aspiration tube 24 to the vicinity of the proximal side of the proximal opening 22 of the guidewire tube 20. The aspiration catheter 10 had a flat portion 40 substantially parallel to the axial direction of the aspiration lumen 24a, at the outer surface of a part of the aspiration tube 24, and the proximal opening 22 of the guidewire tube 20 was located at the flat portion 40. In addition, the aspiration lumen 24a of the aspiration catheter 10 was substantially circular in sectional shape in a direction orthogonal to the axial direction at a distal-side portion not arranged parallel to the guidewire lumen 20a, and had the cut-out circular shape (a shape obtained by cutting out a part of a circular shape) as the cross-sectional shape in a direction orthogonal to the axial direction at a distal-side portion arranged parallel to the guidewire lumen 20a.

The aspiration tube 24 was provided, on the proximal side of a part corresponding to the flat portion 40, with a proximal-side slant portion 36 increasing in outside diameter toward the proximal side. In addition, the aspiration tube 24 was provided, on the distal side of the part corresponding to the flat portion 40, with a distal-side slant portion 38 decreasing in outside diameter toward the distal side. The guidewire lumen 20a of the guidewire tube 20 was provided, at a position corresponding to the distal-side slant portion 38, with a slant portion 42 increasing in diameter toward the proximal side.

2. Manufacture of Comparative Example (Aspiration Catheter 10')

Figure 7A:
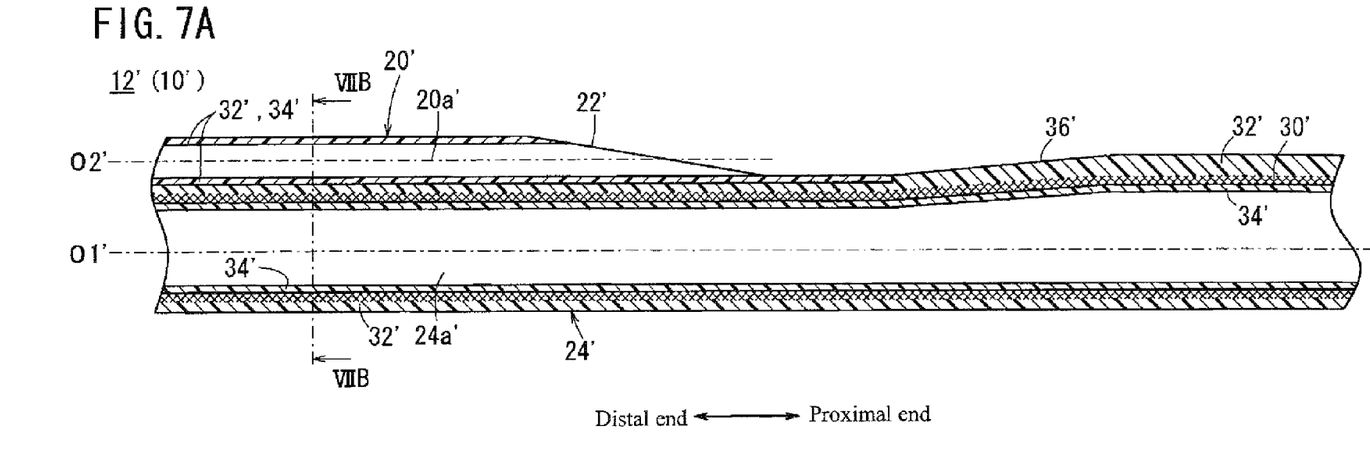
FIG. 7A is a longitudinal cross-sectional view showing, in an enlarged form, a part of an aspiration catheter formed as Comparative Example.
Figure 7B:
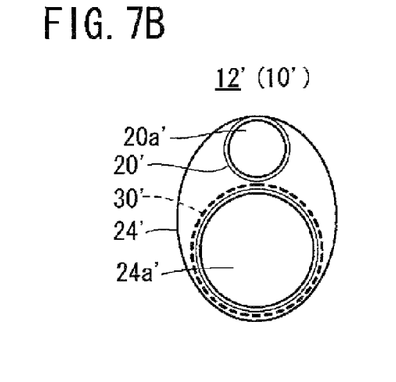
FIG. 7B is a cross-sectional view taken along the section line VIIB-VIIB of FIG. 7A.

FIG. 7A is a side sectional view showing, in an enlarged form, a major part of an aspiration catheter 10' formed as Comparative Example, and FIG. 7B is a sectional view taken along line VIIB-VIIB of FIG. 7A. The aspiration catheter 10' as Comparative Example was manufactured by the same method as for the aspiration catheter of Example, except that a core rod having a circular shape with a diameter of 0.98 mm as sectional shape in a direction orthogonal to the axial direction was used as a core rod for forming an aspiration lumen 24a'. The aspiration catheter 10' thus manufactured was not provided, at an outer surface of a part of the aspiration tube 24', with any flat portion arranged substantially parallel to the axial direction O1' of the aspiration lumen 24a '. The aspiration catheter 10' was circular in sectional shape in a direction orthogonal to the axial direction of the aspiration lumen 24a', over the whole range from the distal end to the proximal end thereof. The aspiration tube 24' of the aspiration catheter 10' was provided, on the proximal side of the vicinity of an opening portion 22' of a guidewire lumen 20a', with a proximal-side slant portion 36' increasing in outside diameter toward the proximal side. However, the aspiration tube 24' was not provided, on the distal side of the vicinity of the opening portion 22' of the guidewire lumen 20a', with any distal-side slant portion decreasing in outside diameter toward the distal side.

3. Evaluation of Sizes

Regarding each of the aspiration catheters 10, 10' manufactured by the methods described in Example and Comparative Example above, the outside diameter of the distal portion (the portion having the guidewire tube 20, 20') of the shaft body 12, 12' was measured by a laser outside diameter measuring instrument (made by KEYENCE CORPORATION). In addition, the distal portion was cut in the direction orthogonal to the axial direction of the shaft body 12, 12', and the cross-sectional area (flow path cross-sectional area) was measured using a microscope (made by KEYENCE CORPORATION). The measurement results are shown in Table 1 below.

TABLE 1

|  | Outside diameter | Flow path sectional area |
| --- | --- | --- |
| Aspiration catheter 10 (Example) | 1.60 mm | 0.80 mm$^2$ |
| Aspiration catheter 10' (Comparative Example) | 1.70 mm | 0.79 mm$^2$ |

As shown in Table 1, the outside diameter of the distal portion of the shaft body 12 of the aspiration catheter 10 of the Example was smaller than that (12') of the aspiration catheter 10' of the Comparative Example, while the aspiration lumen 24a of the aspiration catheter 10 had a flow path cross-sectional area comparable to that of the aspiration lumen 24a' of the aspiration catheter 10'.

4. Evaluation Test of Aspiration Performance

The aspiration catheters 10, 10' were put to an evaluation test of aspiration performance as follows. One end of a two-way stop cock was attached to the hub 16 at the proximal end of the aspiration catheter 10, 10', a 30-mL syringe was attached to the other end of the two-way stop cock, and an aspiration port 14 at the distal end of the aspiration catheter 10, 10' was inserted into a water tank filled with water at 37° C. Next, in the condition where the two-way stop cock was closed, a plunger of the syringe was pulled to a position of 30 mL, and was fixed there. Thereafter, the stop cock was opened to start aspiration, the time point when water was aspirated to a syringe indication of 5 mL was taken as 0 (zero) sec, and the time required for water to be aspirated to a syringe indication of 25 mL was measured. The aspiration catheters 10, 10' manufactured by the methods described in Example and Comparative Example above were put to this test, and aspiration amount per second was calculated for each of the aspiration catheters. The calculation results are shown in Table 2 below.

TABLE 2

|  | Aspiration amount per second |
| --- | --- |
| Aspiration catheter 10 (Example) | 1.64 mL/s |
| Aspiration catheter 10' (Comparative Example) | 1.64 mL/s |

As shown in Table 2, the catheter 10 of the Example was comparable to the catheter 10' of the Comparative Example in the aspiration amount per second. In short, it was verified by the size evaluation and aspiration performance evaluation that the catheter 10 of the Example has a relatively small outside diameter, yet has sufficient aspiration performance.

5. Evaluation of Insertability of Guidewire

In regard of each of the aspiration catheters 10, 10' manufactured by the methods described in the Example and the Comparative Example above, a guidewire 11 was inserted via the distal end of the guidewire lumen 20a, 20a' toward the proximal opening portion 22, 22', and resistance during this process was measured. The term "resistance" here means a calculated value of a force exerted on the guidewire 11 when the guidewire 11 is inserted into the guidewire lumen 20a, 20a' at a predetermined velocity (for example, 500 mm/min). The values of maximum resistance at the time when the guidewire 11 is led out of the opening portion 22, 22' are shown in Table 3 below. In addition, graphs of resistance indicating the behavior of the guidewire 11 during passage of the guidewire 11 through the guidewire lumen 20a, 20a', inclusive of the maximum resistance, are shown in FIG. 8.

TABLE 3

|  | Resistance |
| --- | --- |
| Aspiration catheter 10 (Example) | 23.6 mN |
| Aspiration catheter 10' (Comparative Example) | 32.3 mN |

Figure 8:
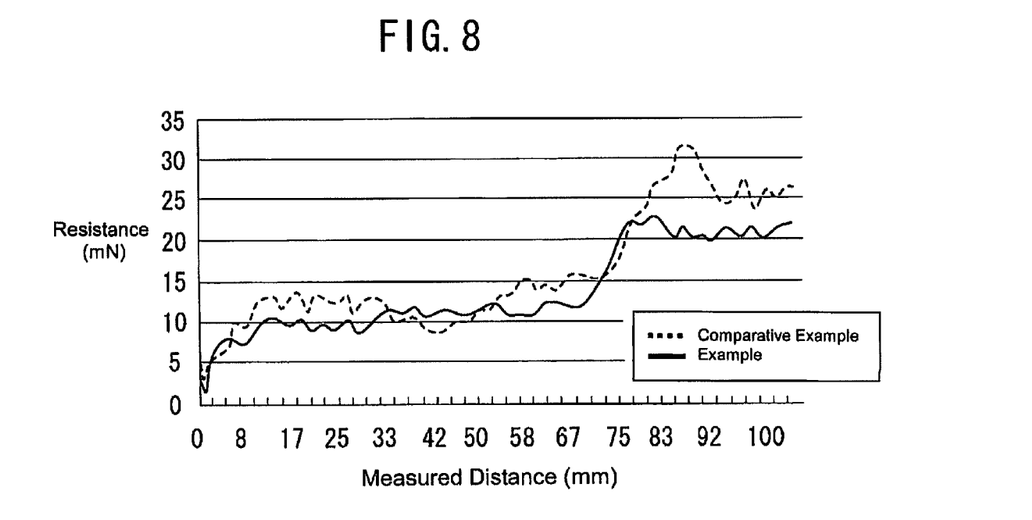
FIG. 8 is a graph showing insertion resistance of guidewires in evaluation of guidewire insertability.

As shown in Table 3 and FIG. 8, the aspiration catheter 10 of the Example was lower than the aspiration catheter 10' of the Comparative Example in resistance at the time when the guidewire 11 is led out via the proximal opening portion 22. In other words, it was made clear that at the proximal opening 22 of the guidewire lumen 20a, the guidewire 11 is inhibited or prevented from being caught on the outer surface of the aspiration tube 24, so that smoother insertion is secured.

6. Evaluation of Aspiration Operation

In the case of the aspiration catheter 10 of the Example, when a syringe was connected to the hub 16 on the proximal side of the aspiration catheter 10 and the plunger of the syringe was pulled to apply a negative pressure, in the condition where the guidewire 11 was inserted in the guidewire lumen 20a, it was possible to perform an aspiration operation via the aspiration portion 14 of the aspiration lumen 24a at the distal end. In addition, while the aspiration operation was stopped between the aspiration operations, it was possible to move the aspiration catheter 10 along the guidewire 11, in the condition where the guidewire 11 was inserted in the guidewire lumen 20a. It was verified from this that in using the aspiration catheter 10 of the Example, it is unnecessary to pull off the guidewire 11 during aspiration process.

The detailed description above describes an aspiration catheter, manner of use and method of manufacturing as disclosed here. The invention is not limited, however, to the precise embodiment and variations described above and illustrated in the drawing figures. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. An aspiration catheter comprising:
an aspiration tube possessing a proximal end, a distal end and an aspiration lumen connectable to a source of negative pressure to aspirate a foreign body from inside a living body, the aspiration lumen extending continuously from the distal end to the proximal end, the aspiration lumen opening to the proximal end of the aspiration tube and opening to the distal end of the aspiration tube, the aspiration tube having a longitudinal extent in which the aspiration tube extends from the distal end to the proximal end;
a guidewire tube fixed to the aspiration tube, the guidewire tube possessing a proximal end, a distal end and a guidewire lumen extending continuously from the distal end of the guidewire tube to the proximal end of the guidewire tube, the guidewire lumen opening to a proximal opening at the proximal end of the guidewire tube and opening to a distal opening at the distal end of the guidewire tube, at least a portion of the guidewire tube being parallel to the aspiration tube and possessing a longitudinal extent less than the longitudinal extent of the aspiration tube;
the aspiration tube possessing an outer surface, one circumferential portion of the outer surface of the aspiration tube possessing a cylindrical shape defined by a radius of curvature, the one circumferential portion of the outer surface of the aspiration tube extending over at least a portion of the longitudinal extent of the aspiration tube;
an other circumferential portion of the outer surface of the aspiration tube not possessing said cylindrical shape defined by said radius of curvature so that the shape of the other circumferential portion of the outer surface of the aspiration tube differs from the shape of the one circumferential portion of the outer surface of the aspiration tube, the other circumferential portion of the outer surface of the aspiration tube extending over said portion of the longitudinal extent of the aspiration tube; and
the proximal opening of the guidewire lumen being circumferentially aligned with the other circumferential portion of the outer surface of the aspiration tube so that the proximal opening of the guidewire lumen is located at the other circumferential portion of the outer surface of the aspiration tube.

2. The aspiration catheter according to claim 1, wherein one portion of the aspiration lumen proximal of the other circumferential portion of the outer surface of the aspiration tube possesses a circular cross-sectional shape in a direction orthogonal to an axis of the aspiration lumen, and an other portion of the aspiration lumen which axially overlaps the other circumferential portion of the outer surface of the aspiration tube possesses a cross-section, a part of the cross-section of the other portion of the aspiration lumen being curved and a remaining part of the cross-section of the other portion of the aspiration lumen being flat.

3. The aspiration catheter according to claim 1, wherein the other circumferential portion of the outer surface of the aspiration tube is flat.

4. The aspiration catheter according to claim 1, wherein the aspiration tube includes a further circumferential portion positioned proximally of the other circumferential portion of the outer surface of the aspiration tube, the further circumferential portion of the outer surface of the aspiration tube is inclined so that an outside diameter of the aspiration tube increases toward the proximal end of the aspiration tube.

5. The aspiration catheter according to claim 4, wherein the guidewire lumen includes, at a position axially overlapping the distal-side slant portion, a slant portion that is inclined so as to increase in outer diameter toward the proximal end of the guidewire tube.

6. The aspiration catheter according to claim 1, wherein the aspiration tube includes a further circumferential portion of the outer surface of the aspiration tube positioned distally of the other circumferential portion of the outer surface of the aspiration tube, the further circumferential portion of the outer surface of the aspiration tube constituting a distal-side slant portion which is inclined so that an outside diameter of the aspiration tube in the distal-side slant portion decreases toward the distal end of the aspiration tube.

7. The aspiration catheter according to claim 1, wherein the other circumferential portion of the outer surface of the aspiration tube also includes a groove portion continuous with the proximal opening of the guidewire lumen and extending in an axial direction of the aspiration tube.

8. The aspiration catheter according to claim 7, wherein the groove portion communicates with the guidewire lumen and is gradually inclined so that a depth of the groove portion gradually increase toward the distal end of the aspiration tube.

9. The aspiration catheter according to claim 1, wherein the proximal opening of the guidewire lumen is obliquely oriented relative to a central axis of the guidewire tube.

10. The aspiration catheter according to claim 1, wherein the other circumferential portion of the outer surface of the aspirator tube not possessing the cylindrical shape is a flat portion, the outer surface of the aspiration tube also comprising a distal-side slant portion arranged distal of the flat portion and on a side of the aspiration tube to which the guidewire is fixed to the aspiration tube, the distal-side slant portion of the outer surface of the aspiration tube slanting so that an outer diameter of the outer surface of the aspiration tube in the distal-side slant portion decreases towards the distal end of the aspiration tube.

11. An aspiration catheter comprising:
an aspiration tube possessing a proximal end, a distal end and an aspiration lumen, the aspiration lumen extending through the aspiration tube and opening to both the proximal end of the aspiration tube and the distal end of the aspiration tube, the aspiration tube having a longitudinal extent in which the aspiration tube extends from the distal end to the proximal end, the aspiration tube also possessing an axis and an outer surface;
a guidewire tube fixed to the aspiration tube, with at least a portion of the guidewire tube positioned parallel to the aspiration tube, the guidewire tube possessing a proximal end, a distal end and a guidewire lumen extending through the guidewire tube, the guidewire lumen opening to a proximal opening at the proximal end of the guidewire tube and opening to a distal opening at the distal end of the guidewire tube, the proximal opening of the guidewire lumen being positioned distally of the proximal end of the aspiration tube;
the aspiration tube possessing one longitudinally extending portion having a cross-section orthogonal to the axis of the aspiration tube, one circumferential portion of said cross-section being flat so that the outer surface of the aspiration tube in the one circumferential portion is a flat outer surface, and a remaining circumferential portion of said cross-section being curved and forming part of a circle so that the outer surface of the aspiration tube in the remaining circumferential portion is a curved outer surface; and
the proximal opening of the guidewire lumen being circumferentially aligned with the flat outer surface of the aspiration tube so that the proximal opening of the guidewire lumen opens to the flat outer surface of the aspiration tube.

12. The aspiration catheter according to claim 11, wherein one portion of the aspiration lumen proximal of the one longitudinally extending portion possesses a circular cross-sectional shape in a direction orthogonal to an axis of the aspiration lumen, and an other portion of the aspiration lumen which axially overlaps the one longitudinally extending portion possesses a cross-section, a part of the cross-section of the other portion of the aspiration lumen being curved and a remaining part of the cross-section of the other portion of the aspiration lumen being flat.

13. The aspiration catheter according to claim 11, wherein the flat outer surface of the one longitudinally extending portion of the aspiration tube also includes a groove portion continuous with the proximal opening of the guidewire lumen and extending in an axial direction of the aspiration tube.

14. The aspiration catheter according to claim 11, wherein the outer surface of the aspiration tube comprises a distal-side slant portion arranged along a side of the outer surface to which the guidewire tube is fixed, the distal-side slant portion of the outer surface of the aspiration tube being inclined so that an outer diameter of the outer surface of the aspiration tube decreases towards the distal end of the aspiration tube.

15. An aspiration catheter comprising: an aspiration tube possessing a proximal end, a distal end and an aspiration lumen extending between and being open at the distal and proximal ends of the aspiration tube, the aspiration tube possessing an outer surface; a guidewire tube bonded to the outer surface of the aspiration tube on a distal end portion of the aspiration tube, at least a portion of the guidewire tube being parallel to the aspiration tube, and a guidewire lumen extending through the guidewire tube and opening at a proximal opening located at a proximal end of the guidewire tube; the outer surface of the aspiration tube having a flat portion such that the outer surface of the flat portion is parallel to an axial direction of the aspiration lumen; the proximal opening of the guidewire lumen is located at the flat portion of the outer surface of the aspiration tube; and wherein one portion of the aspiration lumen proximal of the flat portion of the outer surface of the aspiration tube possesses a circular cross-sectional shape in a direction orthogonal to an axis of the aspiration lumen, and an other portion of the aspiration lumen which axially overlaps the flat portion of the outer surface of the aspiration tube possesses a cross-section, a part of the cross-section of the other portion of the aspiration lumen being curved and a remaining part of the cross-section of the other portion of the aspiration lumen being flat.

16. The aspiration catheter according to claim 15, wherein the aspiration tube includes a slanted outer surface portion positioned proximally of the flat portion of the aspiration tube, the slanted outer surface portion being inclined so that an outside diameter of the aspiration tube in the slanted outer surface portion increases toward the proximal end of the aspiration tube.

17. The aspiration catheter according to claim 15, wherein the aspiration tube includes a distal-side slant portion positioned distally of the flat portion of the outer surface of the aspiration tube, the distal-side slant portion being inclined so that an outside diameter of the aspiration tube in the distal-side slant portion decreases toward the distal end of the aspiration tube.

18. The aspiration catheter according to claim 17, wherein the guidewire lumen includes, at a position axially overlapping the distal-side slant portion, a slant portion that is inclined so as to increase in outer diameter toward a proximal end of the guidewire tube.

19. The aspiration catheter according to claim 15, wherein the flat portion of the outer surface of the aspiration tube also includes a groove portion continuous with the proximal opening of the guidewire lumen and extending in an axial direction of the aspiration tube.

20. The aspiration catheter according to claim 19, wherein the groove portion communicates with the guidewire lumen and is gradually inclined so that a depth of the groove portion gradually increase toward the distal end of the aspiration tube.

21. The aspiration catheter according to claim 15, wherein the proximal opening of the guidewire lumen is obliquely oriented relative to a central axis of the guidewire lumen.

22. The aspiration catheter according to claim 15, wherein the flat portion of the outer surface of the aspiration tube is arranged between a distal-side slant portion and a proximal-side slant portion, the distal-side slant portion and the proximal-side slant portion being arranged along a portion of the outer surface of the aspiration tube to which the guidewire is bonded, the distal-side slant portion and the proximal-side slant portion each being inclined so that an outer diameter of the outer surface of the aspiration tube in the distal-side slant portion and an outer diameter of the outer surface of the aspiration tube in the proximal-side slant portion decreases towards the distal end portion of the aspiration tube.

* * * * *